United States Patent
Hsu et al.

(10) Patent No.: US 8,136,394 B2
(45) Date of Patent: Mar. 20, 2012

(54) METHODS AND APPARATUS FOR ANALYZING A DOWNHOLE FLUID

(75) Inventors: Kai Hsu, Sugar Land, TX (US);
Emmanuel Desroques, Fuchinobe (JP);
Kentaro Indo, Alberta (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 515 days.

(21) Appl. No.: 12/425,912

(22) Filed: Apr. 17, 2009

(65) Prior Publication Data
US 2010/0263442 A1   Oct. 21, 2010

(51) Int. Cl.
*E21B 49/10* (2006.01)

(52) U.S. Cl. .................................................. 73/152.24

(58) Field of Classification Search ............... 73/152.24, 73/152.38, 152.42; 702/6–9
See application file for complete search history.

(56) References Cited

U.S. PATENT DOCUMENTS

| | | | |
|---|---|---|---|
| 4,782,695 A | 11/1988 | Glotin et al. | |
| 5,167,149 A | 12/1992 | Mullins et al. | |
| 5,329,811 A | 7/1994 | Schultz et al. | |
| 5,473,939 A | 12/1995 | Leder et al. | |
| 5,635,631 A | 6/1997 | Yesudas et al. | |
| 5,741,962 A | 4/1998 | Birchak et al. | |
| 6,128,949 A | 10/2000 | Kleinberg | |
| 6,223,588 B1 | 5/2001 | Burgass et al. | |
| 6,334,489 B1 | 1/2002 | Shwe et al. | |
| 6,490,916 B1 | 12/2002 | Goodwin et al. | |
| 6,501,072 B2 | 12/2002 | Mullins et al. | |
| 6,609,568 B2 * | 8/2003 | Krueger et al. | 166/250.07 |
| 6,758,090 B2 | 7/2004 | Bostrom et al. | |
| 6,792,798 B2 | 9/2004 | Liang | |
| 7,002,142 B2 | 2/2006 | Mullins et al. | |
| 7,075,063 B2 | 7/2006 | Dong et al. | |
| 7,216,533 B2 | 5/2007 | McGregor et al. | |
| 7,234,521 B2 | 6/2007 | Shammai et al. | |
| 7,346,460 B2 | 3/2008 | DiFoggio et al. | |
| 7,458,252 B2 | 12/2008 | Freemark et al. | |
| 7,461,547 B2 | 12/2008 | Terabayashi et al. | |
| 7,788,972 B2 * | 9/2010 | Terabayashi et al. | 73/152.27 |
| 2009/0078036 A1 | 3/2009 | Terabayashi et al. | |
| 2009/0078412 A1 | 3/2009 | Kanayama et al. | |

OTHER PUBLICATIONS

Proett, Mark A., New Wireline Formation Testing Tool with Advanced Sampling Technology, Apr. 2001 SPE Reservoir Evaluation & Engineering, pp. 76-87.
Michaels, John et al., Advances in Wireline Formation Testing, SPWLA 36th Annual Logging Symposium, Jun. 26-29, 1995.
Lee, Jaedong et al., Using PV Tests for Bubble Point Pressures and Quality Control, SPWLA 44th Annual Logging Symposium, Jun. 22-25, 2003.

* cited by examiner

*Primary Examiner* — John Fitzgerald
(74) *Attorney, Agent, or Firm* — David J Smith

(57) ABSTRACT

Methods and apparatuses for analyzing a downhole fluid are disclosed. An example method may involve the steps of admitting the downhole fluid in a test volume, controllably inducing a pressure change in the test volume based on at least one prescribed rate, measuring pressures in the test volume at a plurality of times, using the pressures measured at the plurality of times to determine a time at which an actual rate of the pressure change in the test volume deviates from the at least one prescribed rate, and detecting an occurrence of phase transition of the downhole fluid based on the determined time.

20 Claims, 8 Drawing Sheets

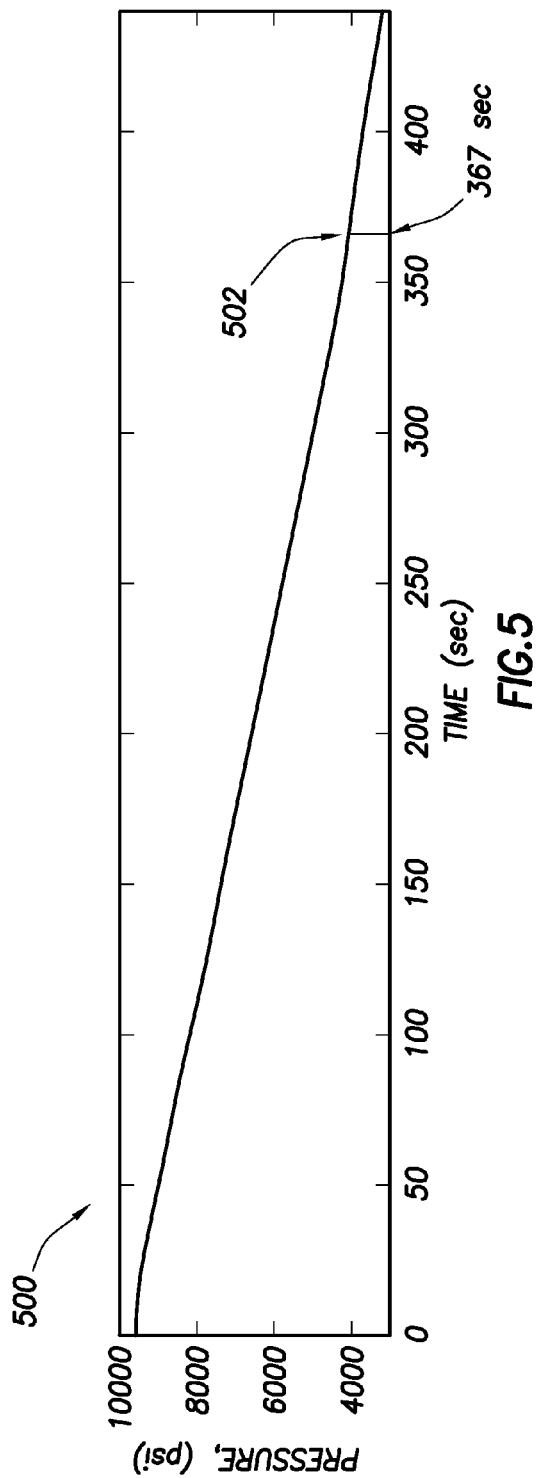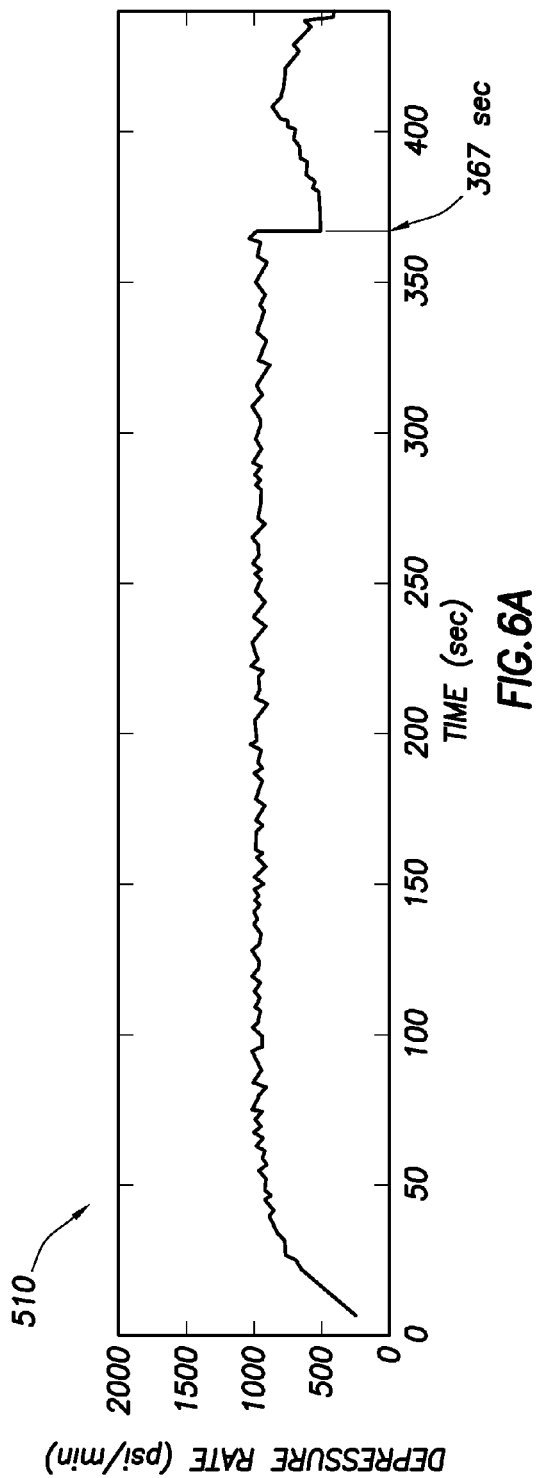

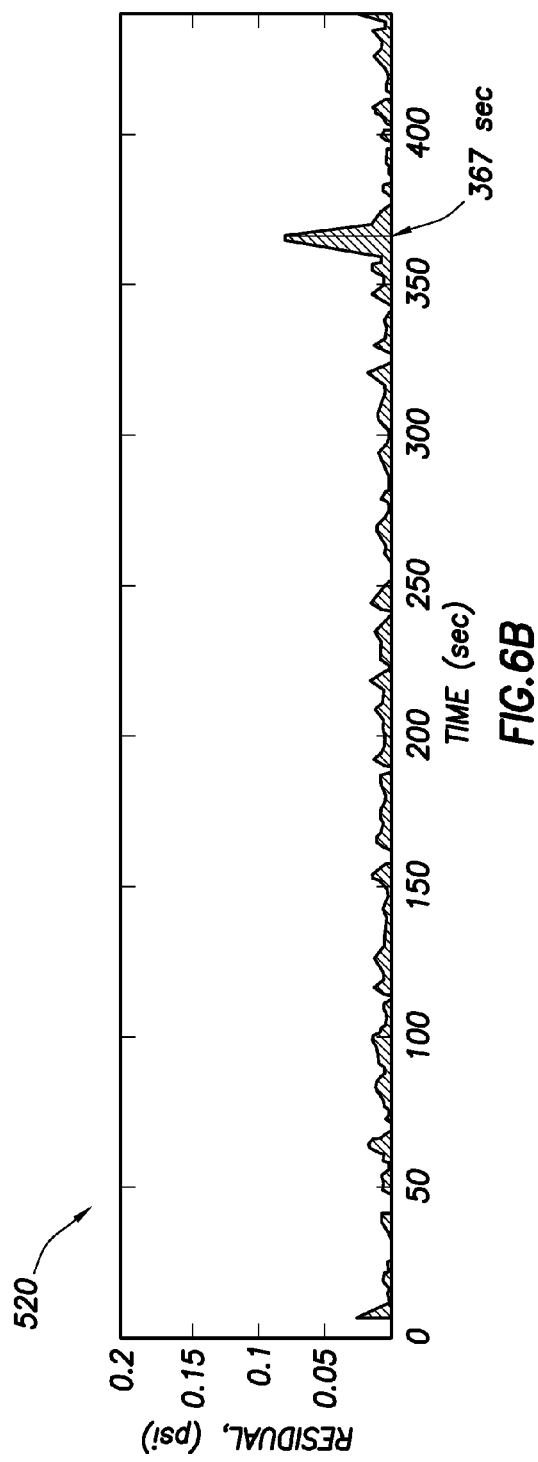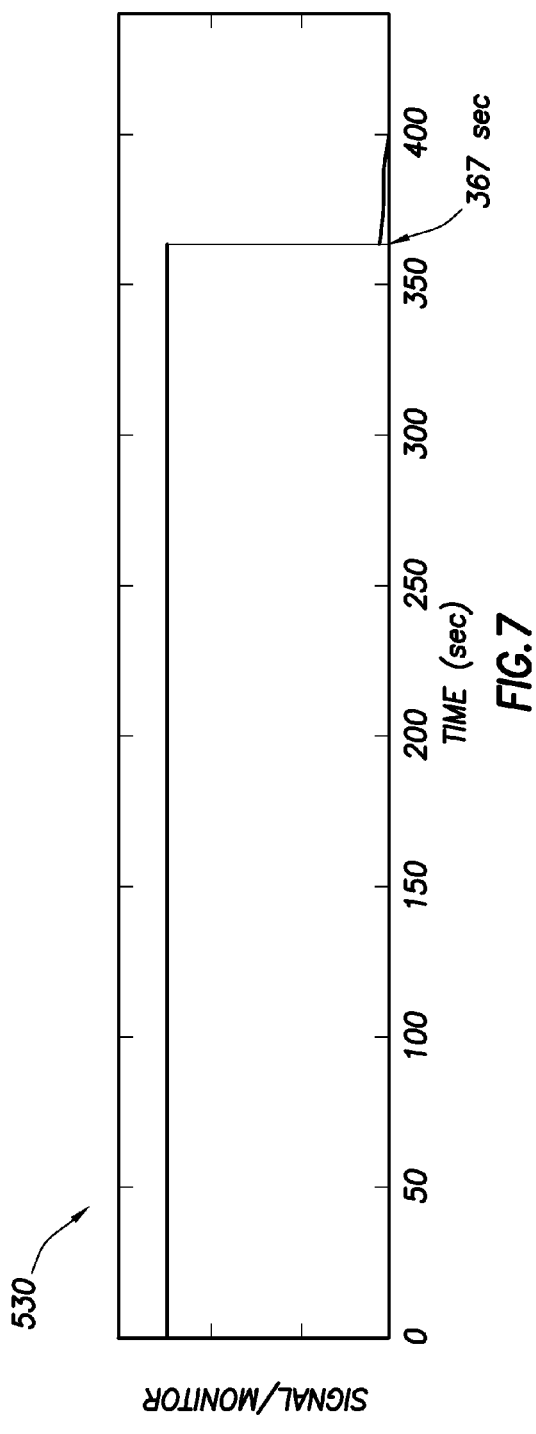

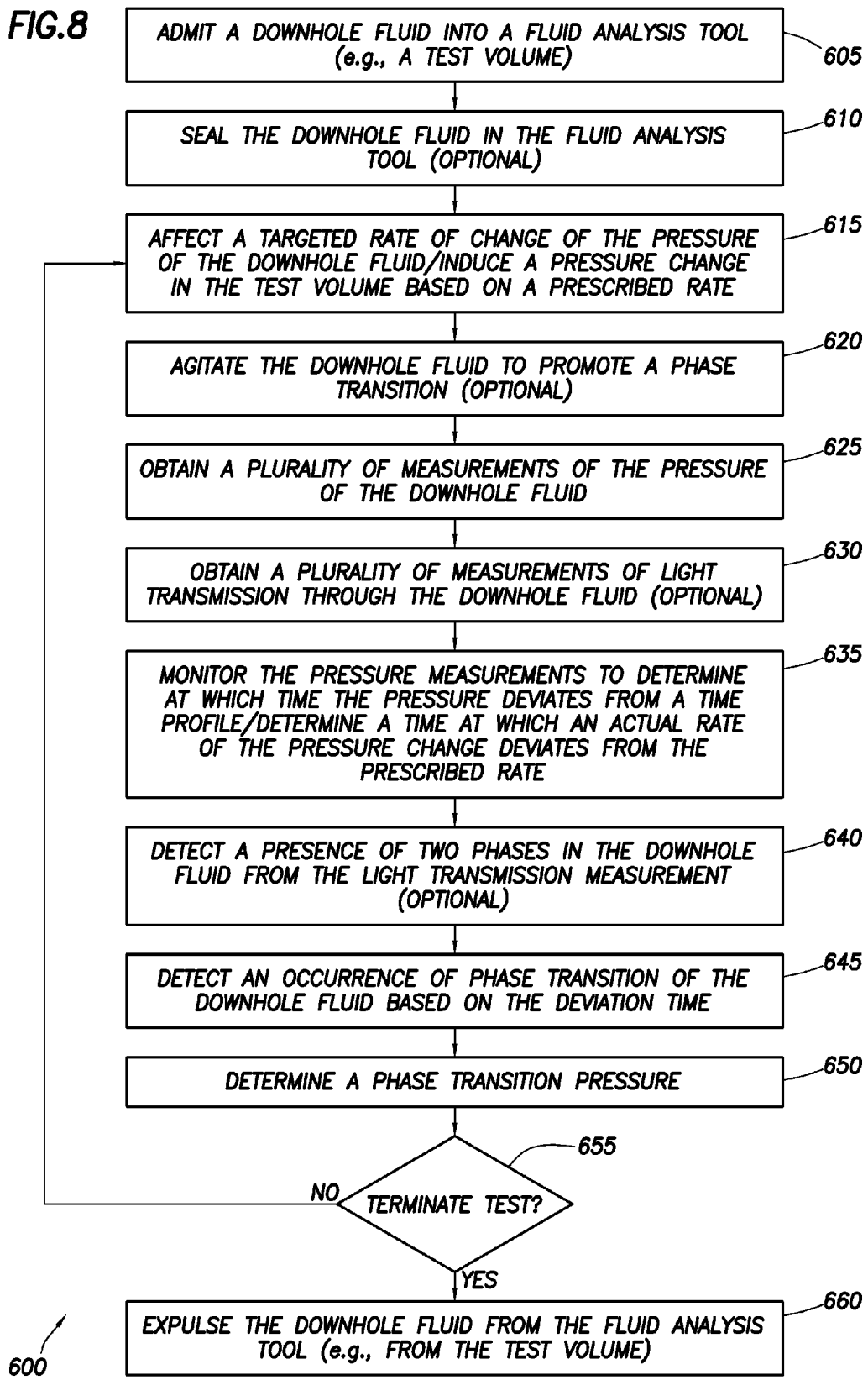

METHODS AND APPARATUS FOR ANALYZING A DOWNHOLE FLUID

BACKGROUND OF THE DISCLOSURE

The present disclosure relates to measuring the phase transition pressure of a downhole fluid extracted from a subterranean formation into which a well has been drilled.

It is conventional to investigate the characteristics of downhole fluids contained in underground formations by taking samples and analyzing the samples in a laboratory or in situ. In particular, a downhole fluid characteristic is the phase transition pressure, which may be one of a bubble point pressure, a dew point pressure, or an asphaltene onset pressure.

Some methods and apparatuses may utilize pressure versus volume curves to determine a phase transition pressure. Disclosures of such methods or apparatuses may be found, for example, in U.S. Pat. Nos. 4,782,695; 5,329,811; 5,473,939; 5,635,631; 6,334,489; 7,346,460; and 7,461,547, and U.S. Patent Application publication No. 2009/0078036, the disclosures of which are incorporated herein by reference.

Methods and apparatuses may also utilize variations of a fluid property as a function of pressure to determine a phase transition pressure. Disclosures of such methods or apparatuses may be found, for example, in U.S. Pat. Nos. 5,167,149; 5,741,962; 6,128,949; 6,223,588; 6,501,072; 6,758,090; 6,792,798; 7,002,142 and 7,075,063, the disclosures of which are incorporated herein by reference.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 5 is a graph of a downhole fluid pressure as a function of time according to one or more aspects of the present disclosure.

FIGS. 6A and 6B are graphs of parameters indicative of a curve irregularity as a function of time in relation to the graph shown in FIG. 5.

FIG. 7 is a graph of a downhole fluid property as a function of time according to one or more aspects of the present disclosure.

FIG. 8 is a flow chart of at least a portion of a method of analyzing downhole fluid according to one or more aspects of the present disclosure.

DETAILED DESCRIPTION

Figure 1:
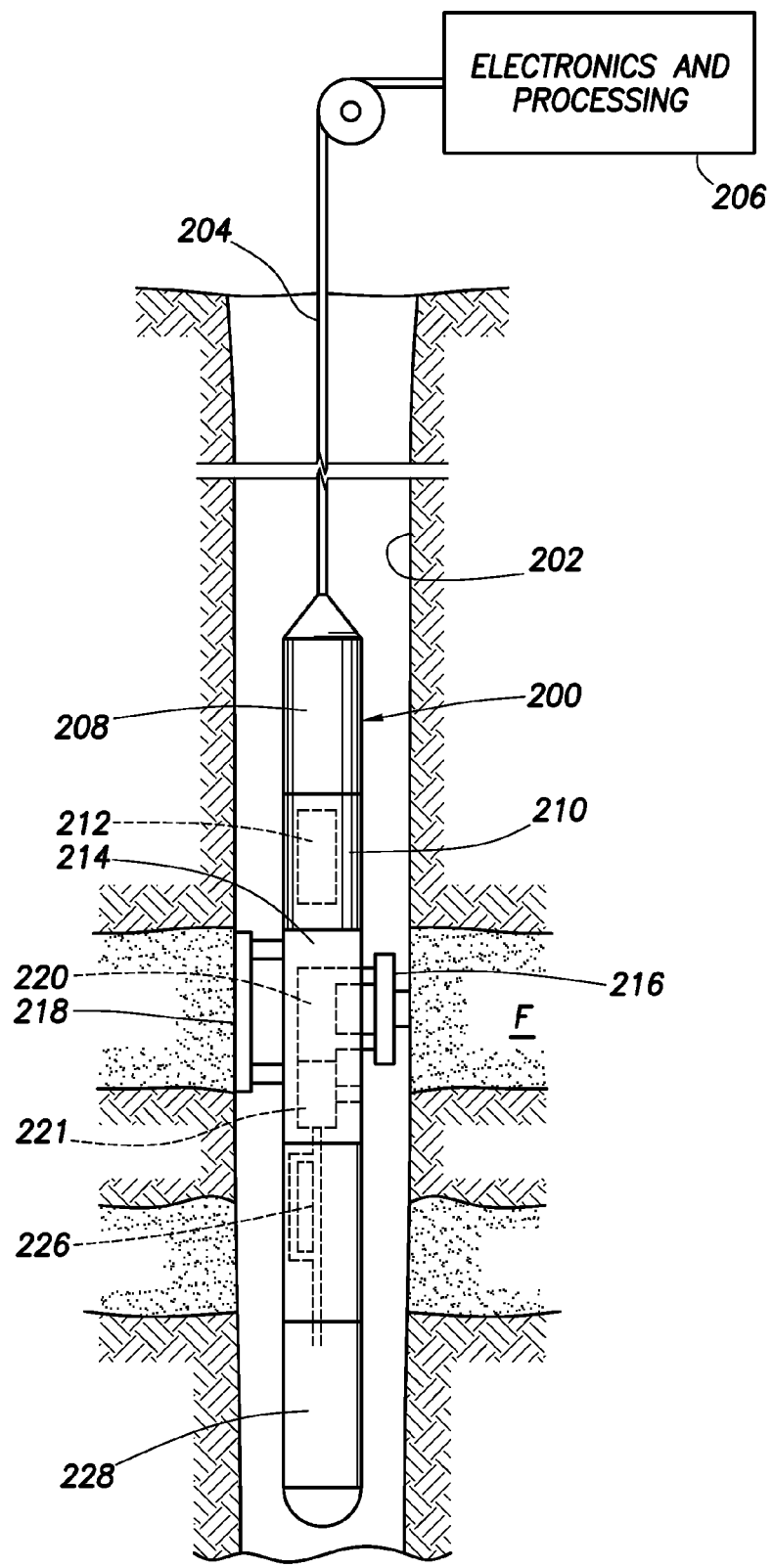
FIG. 1 is a schematic view of a fluid analysis system according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Methods and apparatuses for analyzing downhole fluid are disclosed herein. The methods and apparatuses of the present disclosure may be used to determine phase transition pressures of downhole fluid samples extracted from a subterranean formation into which a well has been drilled. In some cases, the downhole fluid samples may be brought to the surface and analyzed in a laboratory. In other cases, the downhole fluid samples may be analyzed in situ, using a fluid analysis tool lowered in the well.

Some known methods utilize a constant volume expansion rate to determine a phase transition pressure of downhole fluid samples. When using these known methods, it may be difficult to tailor the expansion rate to the downhole fluid compressibility a priori, for example, because the downhole fluid compressibility is typically unknown. Thus, the methods utilizing a constant volume expansion rate may result in large variations of the rate of pressure change of the downhole fluid during the determination of the phase transition pressure. Relatively large rates of pressure change may reduce the accuracy of the measurement of the phase transition pressure of the downhole fluid. Relatively small rates of pressure change may increase the duration of the test performed to measure the phase transition pressure of the downhole fluid.

In the present disclosure, fluid analysis tools are directed to induce a prescribed rate of change of the pressure of the downhole fluid in the fluid analysis tool, for example according to a predetermined pressure versus time profile. Typically, the fluid analysis tools may include a pressure changing device configured to controllably induce a pressure change in the test volume based on at least one prescribed rate. The phase transition pressure may be determined using time data points generated from measured pressures at a plurality of times.

Herein, a predetermined pressure versus time profile may also be referred to as a pressure rate profile. Inducing a prescribed rate of change of the pressure may comprise affecting a prescribed rate of change of the pressure. A prescribed rate of change may also be referred to as a targeted rate of change.

The methods of the present disclosure may not require measuring a volume of the downhole fluid to determine the phase transition pressure of the downhole fluid. The foregoing may be advantageous in some cases, for example when a determination of the downhole fluid volume is difficult to obtain (e.g., is unknown), such as when the downhole fluid is not sealed in a test volume, and/or if a sealed volume enclosure is relatively compliant under pressure compared to the downhole fluid compressibility. However, the volume of the downhole fluid may optionally be estimated and/or measured within the scope of the present disclosure.

Further, the methods of the present disclosure may not require measuring the variations of a fluid property as a function of pressure to determine the phase transition pressure.

The foregoing may be advantageous in some cases, for example to determine a first phase transition pressure from a pressure signature, and to compare the first phase transition pressure to a second phase transition pressure derived from fluid property variations with pressure. Thus, a redundancy of the phase transition pressure measurement may be achieved using a relatively limited number of sensors.

Turning to FIG. 1, an example well site system according to one or more aspects of the present disclosure is shown. The well site may be situated onshore (as shown) or offshore. In particular, a wireline tool 200 may be configured to determine phase transition pressures of downhole fluid samples extracted from a subterranean formation F into which a wellbore 202 has been drilled.

The example wireline tool 200 may be suspended in the wellbore 202 from the lower end of a multi-conductor cable 204 that may be spooled on a winch (not shown) at the Earth's surface. At the surface, the cable 204 may be communicatively coupled to an electronics and processing system 206. The electronics and processing system 206 may include a controller having an interface configured to receive commands from a surface operator. In some cases, the electronics and processing system 206 may further include a processor configured to implement one or more aspects of the methods described herein. The example wireline tool 200 includes an elongated body 208 that may include a telemetry module 210, and a formation tester 214. Although the telemetry module 210 is shown as being implemented separate from the formation tester 214, in some example implementations, the telemetry module 210 may be implemented in the formation tester 214. Further, additional components may also be included in the tool 200.

The formation tester 214 may comprise a selectively extendable fluid admitting assembly 216 and a selectively extendable tool anchoring member 218 that are respectively arranged on opposite sides of the body 208. As shown, the fluid admitting assembly 216 is configured to selectively seal off or isolate selected portions of the wall of the wellbore 202, and to fluidly couple components of the formation tester 214, for example, a pump 221, to the adjacent formation F. Thus, the formation tester 214 may be used to obtain fluid samples from the formation F. The formation tester 214 may also include a fluid sensing unit 220 through which the obtained fluid samples flow. The fluid samples may thereafter be expelled through a port (not shown) into the wellbore or it may be sent to one or more fluid collecting chambers disposed in a sample carrier module 228. In turn, the fluid collecting chambers may receive and retain the formation fluid for subsequent testing at the surface or a testing facility.

In the illustrated example, the formation tester 214 is provided with a fluid isolation and analysis tool 226, fluidly coupled to the fluid admitting assembly 216 and the pump 221. The fluid isolation and analysis tool 226 may include a pressure changing device (not shown) configured to controllably induce or affect a pressure change of a downhole fluids sample extracted from the subterranean formation F into the fluid isolation and analysis tool 226. The fluid isolation and analysis tool 226 may also include a pressure sensor (not shown) configured to measure the pressure of the downhole fluid sample at a plurality of times.

The telemetry module 210 may comprise a downhole control system 212 communicatively coupled to the electrical control and data acquisition system 206. In the illustrated example, the electrical control and data acquisition system 206 and/or the downhole control system 212 may be configured to control the fluid admitting assembly 216 and/or the extraction of fluid samples from the formation F, for example the pumping rate of pump 221. The electrical control and data acquisition system 206 and/or the downhole control system 212 may further be configured to direct the fluid isolation and analysis tool 226 to induce or affect a targeted rate of change of the pressure of the downhole fluid in the fluid isolation and analysis tool 226, for example according to a pressure rate profile.

The electrical control and data acquisition system 206 and/or the downhole control system 212 may still further be configured to analyze and/or process data obtained, for example, from fluid sensing unit 220 or from other downhole sensors (not shown) disposed in the fluid isolation and analysis tool 226, store and/or communicate measurement or processed data to the surface for subsequent analysis. In particular, a phase transition pressure of the downhole fluid in the fluid isolation and analysis tool 226 may be determined using time data points generated from the depressurization or pressurization of the downhole fluid and measured by a pressure sensor (not shown) disposed in the fluid isolation and analysis tool 226.

Figure 2A:
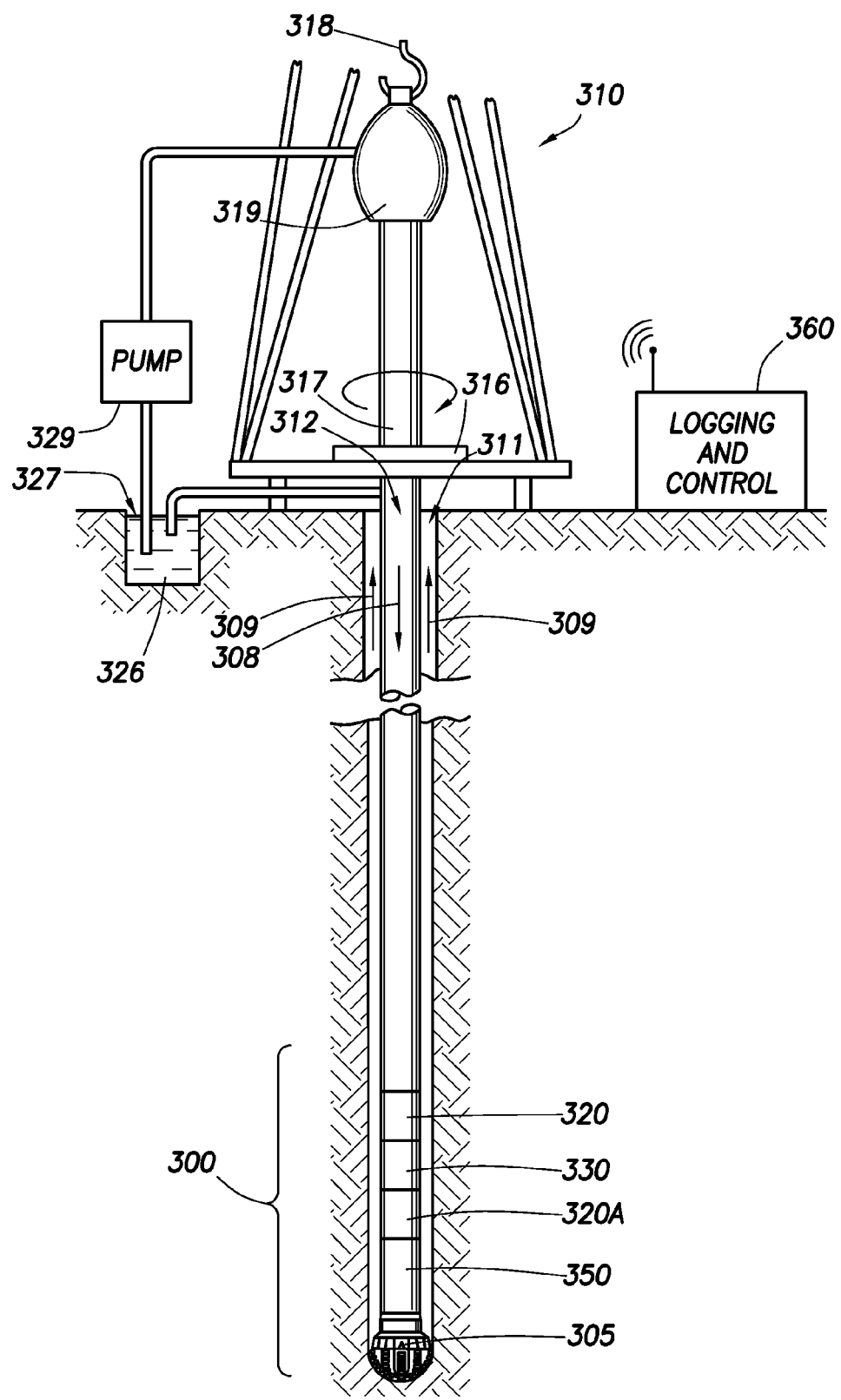
FIG. 2A is a schematic view of another fluid analysis system according to one or more aspects of the present disclosure.
Figure 2B:
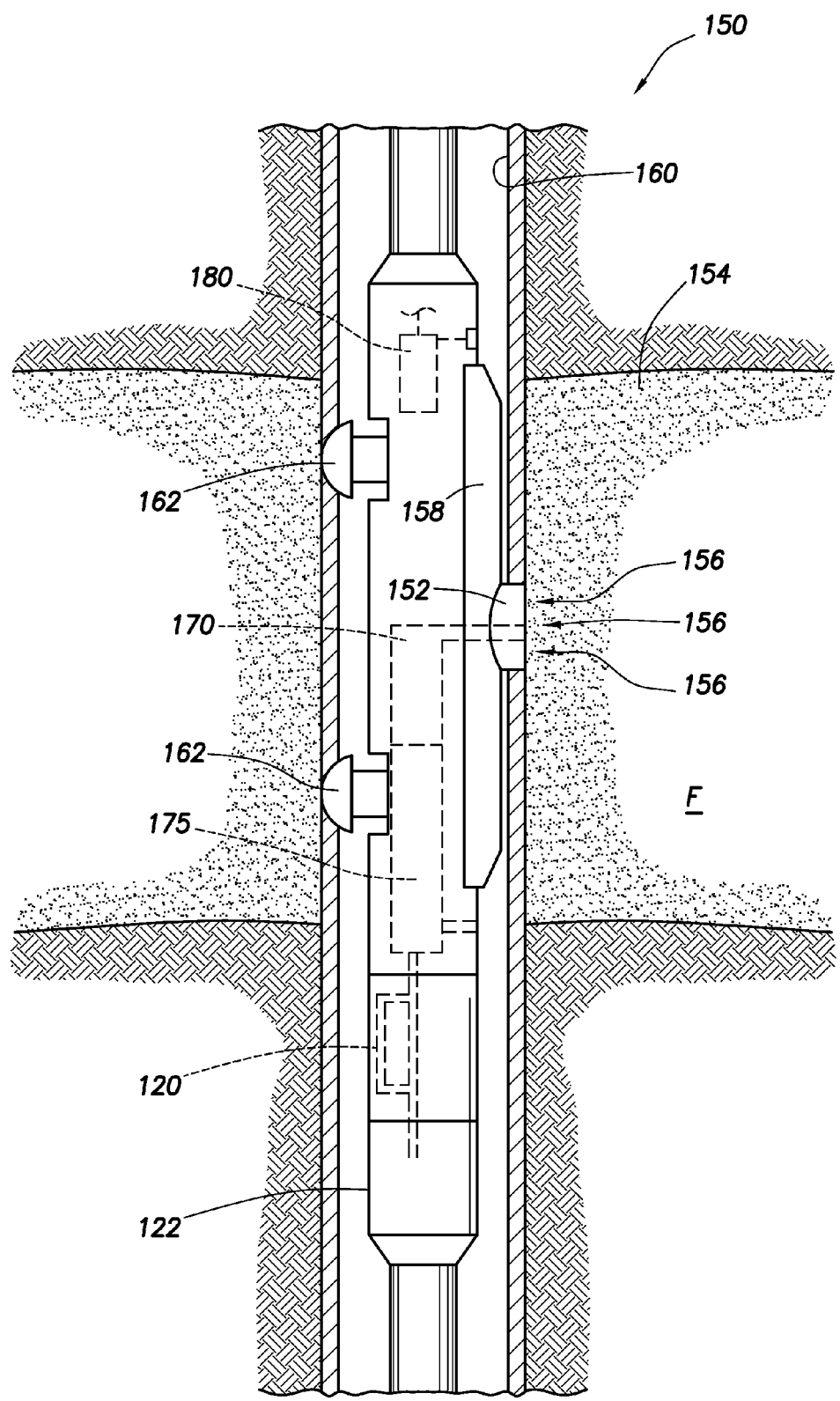
FIG. 2B is a schematic view of a portion of the fluid analysis system shown in FIG. 2A.

Turning to FIGS. 2A and 2B, an example well site system according to one or more aspects of the present disclosure is shown. The well site may be situated onshore (as shown) or offshore. The system comprises a sampling-while drilling device that may be configured to determine phase transition pressures of downhole fluids samples extracted from a subterranean formation F into which a wellbore 311 has been drilled.

Referring to FIG. 2A, the wellbore 311 is drilled through subsurface formations by rotary drilling in a manner that is well known in the art. However, the present disclosure also contemplates others examples used in connection with directional drilling apparatus and methods, as will be described hereinafter.

A drill string 312 is suspended within the wellbore 311 and includes a bottom hole assembly ("BHA") 300 proximate the lower end thereof. The BHA 300 includes a drill bit 305 at its lower end. The surface portion of the well site system includes platform and derrick assembly 310 positioned over the wellbore 311, the assembly 310 including a rotary table 316, kelly 317, hook 318 and rotary swivel 319. The drill string 312 may be rotated by the rotary table 316, which is itself operated by well known means not shown in the drawing. The rotary table 316 engages the kelly 317 at the upper end of the drill string 312. As is well known, a top drive system (not shown) could alternatively be used instead of the kelly 317 and rotary table 316 to rotate the drill string 312 from the surface. The drill string 312 may be suspended from the hook 318. The hook 318 may be attached to a traveling block (also not shown), through the kelly 317 and the rotary swivel 319 which permits rotation of the drill string 312 relative to the hook 318.

In the example of FIG. 2A, the surface system further includes drilling fluid ("mud") 326 stored in a tank or pit 327 formed at the well site. A pump 329 delivers the drilling fluid 326 to the interior of the drill string 312 via a port in the swivel 319, causing the drilling fluid 326 to flow downwardly through the drill string 312 as indicated by the directional arrow 308. The drilling fluid 326 exits the drill string 312 via water courses, or nozzles ("jets") in the drill bit 305, and then circulates upwardly through the annulus region between the outside of the drill string and the wall of the wellbore, as indicated by the directional arrows 309. In this well known manner, the drilling fluid 326 lubricates the drill bit 305 and carries formation cuttings up to the surface, whereupon the drilling fluid 326 may be cleaned and returned to the pit 327 for recirculation. It should be noted that in some implementations, the drill bit 305 may be omitted and the bottom hole assembly 300 may be conveyed via tubing or pipe.

The bottom hole assembly 300 of the illustrated example may include a logging-while-drilling (LWD) module 320, a measuring-while-drilling (MWD) module 330, a rotary-steerable directional drilling system and hydraulically operated motor 350, and the drill bit 305.

The LWD module 320 may be housed in a special type of drill collar, as is known in the art, and may contain one or more well logging instruments. It will also be understood that more than one LWD module may be employed, e.g., as represented at 320A. (References, throughout, to a module at the position of LWD module 320 may alternatively mean a module at the position of LWD module 320A as well.) The LWD module 320 typically includes capabilities for measuring, processing, and storing information, as well as for communicating with the MWD 330. In particular, the LWD module 320 may include a processor configured to implement one or more aspects of the methods described herein. In the present embodiment, the LWD module 320 includes a fluid sampling device as will be further explained below.

The MWD module 330 may also be housed in a special type of drill collar, as is known in the art, and may contain one or more devices for measuring characteristics of the drill string and drill bit. The MWD module 330 further includes an apparatus (not shown) for generating electrical power for the downhole portion of the well site system. Such apparatus typically includes a turbine generator powered by the flow of the drilling fluid 326, it being understood that other power and/or battery systems may be used while remaining within the scope of the present disclosure. In the present example, the MWD module 330 may include one or more of the following types of measuring devices: a weight-on-bit measuring device, a torque measuring device, a vibration measuring device, a shock measuring device, a stick slip measuring device, a direction measuring device, and an inclination measuring device. Optionally, the MWD module 330 may further comprise an annular pressure sensor, and a natural gamma ray sensor. The MWD module 330 typically includes capabilities for measuring, processing, and storing information, as well as for communicating with a logging and control unit 360. For example, the MWD module 330 and the logging and control unit 360 may communicate information either ways (i.e., uplinks and/or downlinks) via systems sometimes referred to as mud pulse telemetry (MPT), and/or wired drill pipe (WDP) telemetry. In some cases, the logging and control unit 360 may include a controller having an interface configured to receive commands from a surface operator.

A sampling-while-drilling device 150 (e.g., similar to the LWD tool 320 in FIG. 2A) is shown in FIG. 2B. The sampling-while-drilling device 150 of FIG. 2B may be of a type described, for example, in U.S. Patent Application Publication No. 2008/0156486, incorporated herein by reference. However, other types of sampling-while-drilling devices may be used to implement the sampling-while-drilling device 150 or portions thereof.

Referring to FIG. 2B, the sampling-while-drilling device 150 may be provided with a stabilizer that may include one or more blades 158 configured to engage a wall 160 of the wellbore 311. The sampling-while-drilling device 150 may be provided with a plurality of backup pistons 162 to assist in applying a force to push and/or move the sampling-while-drilling device 150 against the wall 160 of the wellbore 311 (in FIG. 2A). The configuration of the blade 158, and/or of the backup pistons 162 may be of a type described, for example, in U.S. Pat. No. 7,114,562, incorporated herein by reference. However, other types of blade or piston configurations may be used to implement the sampling-while-drilling device 150 within the scope of the present disclosure.

A fluid admitting assembly 152 may extend from the stabilizer blade 158 of the sampling-while-drilling device 150. The fluid admitting assembly 152 may be configured to selectively seal off or isolate selected portions of the wall 160 of the wellbore 311 (in FIG. 2A) to fluidly couple to an adjacent formation F. Once the fluid admitting assembly 152 fluidly couples to the adjacent formation F, various measurements may be conducted on the adjacent formation F, for example, a pressure parameter may be measured by performing a pretest. Also, a pump 175 may be used to draw downhole fluid 154 from the formation F into the sampling-while-drilling device 150 in a direction generally indicated by arrows 156. The fluid may thereafter be expelled through a port (not shown) into the wellbore, or it may be sent to one or more fluid collecting chambers disposed in a sample carrier module 122, which may receive and retain the formation fluid for subsequent testing at the surface or a testing facility.

Optionally, the sampling-while-drilling device 150 may include a fluid sensing unit 170 through which the obtained fluid samples may flow, and configured to measure properties of the fluid samples extracted from the formation F. It should be appreciated that the fluid sensing unit 170 may include any combination of conventional and/or future-developed sensors within the scope of the present disclosure.

A downhole control system 180 may be configured to control the operations of the sampling-while-drilling device 150. In particular, the downhole control system 180 may be configured to control the extraction of fluid samples from the formation F, for example, via the pumping rate of the pump 175. The downhole control system 180 may still further be configured to analyze and/or process data obtained, for example, from fluid sensing unit 170 or other downhole sensors (not shown), store and/or communicate measurement or processed data to the surface for subsequent analysis. In particular, the downhole control system 180 may include a processor configured to implement one or more aspects of the methods described herein.

The sampling-while-drilling device 150 may be provided with a fluid isolation and analysis tool 120, fluidly coupled to the fluid admitting assembly 152 and the pump 175. The fluid isolation and analysis tool 120 may include a pressure changing device (not shown) configured to controllably induce or affect a pressure change of a downhole fluid sample extracted from the subterranean formation F into the fluid isolation and analysis tool 120. The logging and control unit 360 (in FIG. 2A) and/or the downhole control system 180 may include a controller configured to direct the fluid isolation and analysis tool 120 to induce or affect a targeted rate of change of the pressure of the downhole fluid in the fluid isolation and analysis tool 120, for example according to a pressure rate profile. The fluid isolation and analysis tool 120 may further include a pressure sensor (not shown) configured to measure the pressure of the downhole fluid sample at a plurality of times. The logging and control unit 360 (in FIG. 2A) and/or the downhole control system 180 may include a processor (not shown) configured to analyze and/or process data obtained by the pressure sensor (not shown) disposed in the fluid isolation and analysis tool 120. In particular, a phase transition pressure of the downhole fluid in the fluid isolation and analysis tool 120 may be determined using time data points generated from pressure measurements of the downhole fluid.

While the wireline tool 200 (in FIG. 1) and the sampling-while-drilling device 150 (in FIG. 2B) are depicted having one fluid admitting assembly, a plurality of fluid admitting assemblies may alternatively be provided on the wireline tool 200 and/or the sampling-while-drilling device 150. In particular, the fluid admitting assembly of the wireline tool 200 (in FIG. 1) and/or the sampling-while-drilling device 150 (in FIG. 2B) may be implemented with a guarded or focused fluid admitting assembly, for example, as shown in U.S. Pat. No. 6,964,301, incorporated herein by reference. In these cases, the fluid isolation and analysis tool 226 (in FIG. 1) and/or the fluid isolation and analysis tool 120 (in FIG. 2B) may be fluidly coupled to a central inlet of the guarded or focused fluid admitting assembly.

Figure 3:
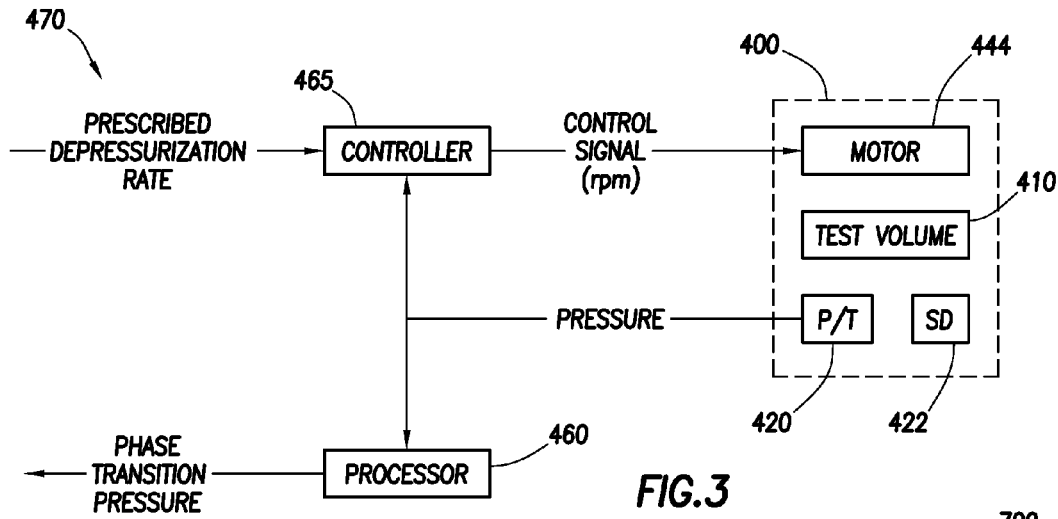
FIG. 3 is a diagram of a phase transition measurement tool according to one or more aspects of the present disclosure.

Turning to FIG. 3, a diagram of a phase transition measurement tool 470 according to one or more aspects of the present disclosure is shown. For the sake of brevity and clarity, only a portion of the components of the phase transition measurement tool 470 are depicted in FIG. 3. In particular, the phase transition measurement tool 470 may comprise a pressure changing device configured to controllably induce or affect a pressure change in a test volume 410 based on at least one prescribed rate, or in other words, the pressure changing device may be directed to induce or affect a targeted rate of change of the pressure of the downhole fluid in the phase transition measurement tool 470, for example according to a pressure rate profile. In some cases, at least portions of the phase transition measurement tool 470 may be configured to be lowered in the wellbore using one or more of a wireline cable, a drill string, and a tubing.

The phase transition measurement tool 470 may comprise a fluid isolation and analysis tool 400 such as the fluid isolation and analysis tool 226 (in FIG. 1) or the fluid isolation and analysis tool 120 (in FIG. 2A). The fluid isolation and analysis tool 400 may be of a type described, for example, in U.S. Pat. Nos. 7,458,252, or 7,461,547, both incorporated herein by reference. The fluid isolation and analysis tool 400 may also be of a type described herein in FIGS. 4A and 4B. In particular, the fluid isolation and analysis tool 400 may comprise an electric motor 444 operatively coupled to the test volume 410 and configured to alter the pressure of a downhole fluid in the test volume 410. The fluid isolation and analysis tool 400 may also comprise a pressure sensor 420 configured to measure pressures in the test volume 410.

The phase transition measurement tool 470 may comprise a controller 465 communicatively coupled to the pressure sensor 420. In cases where the fluid isolation and analysis tool 400 is part of a downhole tool (as shown in FIGS. 1, 2A and 2B), the controller 465 may be preferably, but not necessarily, implemented downhole (e.g., provided by the downhole control system 212 of FIG. 1, or by the downhole control system 180 of FIG. 2B). The controller 465 may be configured to induce the pressure change in the test volume 410 based on the measured pressures in the test volume 410. For example, the controller may be provided with discrete data $s(t_0)$, $s(t_1)$, $s(t_2)$, ..., $s(t_n)$, indicative of prescribed or targeted rates of pressure change, for example according to a predetermined pressure rate profile function of a plurality of times $t_1$, $t_2$, ..., $t_n$. The prescribed or targeted rates may be retrieved from a computer readable medium (not shown), or entered by an operator via an interface (such as provided by the electronics and processing system 206 of FIG. 1, or by the logging and control unit 360 of FIG. 2A). The pressure sensor 420 may be configured to measure the pressure in the test volume 410 at a plurality of times and communicate the measured pressures $p(t_0)$, $p(t_1)$, $p(t_2)$, ..., $p(t_n)$ to the controller 465. The controller 465 may be configured to determine actual rates of the pressure change $y(t_0)$, $y(t_1)$, $y(t_2)$, ..., $y(t_n)$ in the test volume 410 from the measured pressures $p(t_0)$, $p(t_1)$, $p(t_2)$, ..., $p(t_n)$. For example, the actual rates of the pressure change $y(t_0)$, $y(t_1)$, $y(t_2)$, ..., $y(t_n)$ may be determined by fitting a curve to a portion of the measured pressures at the plurality of times, and determining a curve slope. The fitting may be performed using a conventional least-squares algorithm such as the Savitzky-Golay filter (for example a second order filter), or using a robust iterative re-weighted least algorithm. The controller 465 may further be configured to determine an error signal $e(t_0)$, $e(t_1)$, $e(t_2)$, ..., $e(t_n)$ between the actual rates (or monitored rates) and the prescribed rates (or targeted rates). For example, the error signal may be computed as follows:

$$e(t_i) = s(t_i) - y(t_i)\ i = 0, 1, 2, \ldots, n$$

The controller 465 may still further be configured to drive the motor 444 via a control signal $u(t_0)$, $u(t_1)$, $u(t_2)$, ..., $u(t_n)$, such as a prescribed angular speed (or rotations per minutes rpm). The controller 465 may be configured to execute instructions stored on a computer readable medium (not shown), that, when executed, cause the fluid isolation and analysis tool 400 to induce or affect targeted rates of change of the pressure $s(t_0)$, $s(t_1)$, $s(t_2)$, ..., $s(t_n)$ of the downhole fluid in the test volume 410. For example, the angular speed of the motor 444 may be determined such that the rate pressure change of the downhole fluid in the test volume 410 resulting from the motor rotation reduces the magnitude of the error signal $e(t_i)$. The controller 465 may be configured to implement a feedback control of the motor 444 using a proportional-integral-derivative controller (PID controller), as is commonly used in industrial control systems. The control signal $u(t_0)$, $u(t_1)$, $u(t_2)$, ..., $u(t_n)$ may be computed using the following iterative form:

$$u(t_0) = u(t_1) = u_0$$

$$u(t_i) = u(t_{i1}) + k_1 e(t_i) + k_2(e(t_i) - e(t_{i1})) + k_3(e(t_i) - 2e(t_{i1}) + e(t_{i2}))\ i = 2, \ldots, n$$

where $u_0$ is an initial angular speed, $k_1$, $k_2$, and $k_3$ are constant gains. The values of $k_1$, $k_2$, and $k_3$ may be tuned, for example using tuning procedures known in the art.

The phase transition measurement tool 470 may comprise a processor 460, communicatively coupled to the pressure sensor 420. In cases where the fluid isolation and analysis tool 400 is part of a downhole tool (as shown in FIGS. 1, 2A and 2B), the processor 460 may be implemented at the Earth's surface (e.g., provided by the electronics and processing system 206 of FIG. 1), or downhole (e.g., provided by the downhole control system 180 of FIG. 2B). The processor 460 may be configured to determine, based on the pressures measured by the pressure sensor 420, a time at which an actual rate of the pressure change in the test volume deviates from a prescribed rate. The processor 460 may further be configured to detect an occurrence of phase transition of the downhole fluid based on the determined time. For example, the processor 460 may be configured to execute instructions stored on a computer readable medium (not shown), that, when executed, cause the processor 460 to perform the method described in FIG. 8 herein. The processor 460 may further be configured to determine a phase transition pressure from the detected occurrence of phase transition, and at least a portion of the pressures measured by the pressure sensor 420. The phase transition pressure may then be recorded or stored on a computer readable medium (not shown), and/or printed or displayed on a log.

Optionally, the phase transition measurement tool 470 may comprise a fluid sensor 422 configured to measure a property of the downhole fluid. The processor 460 may be configured to detect a presence of two phases in the downhole fluid using the downhole fluid properties measured by the fluid sensor 422. For example, the processor 460 may be configured to execute instructions stored on a computer readable medium (not shown), that, when executed, cause the processor 460 to measure first and second parameter values indicative of light transmission through the downhole fluid. The first and second parameters values may be compared to detect a reduction of light transmission level. For example, the reduction of light transmission level may be indicative of the presence (e.g., the emergence) of gas bubbles in the fluid, as further described in relation to FIG. 7.

Figure 4B:
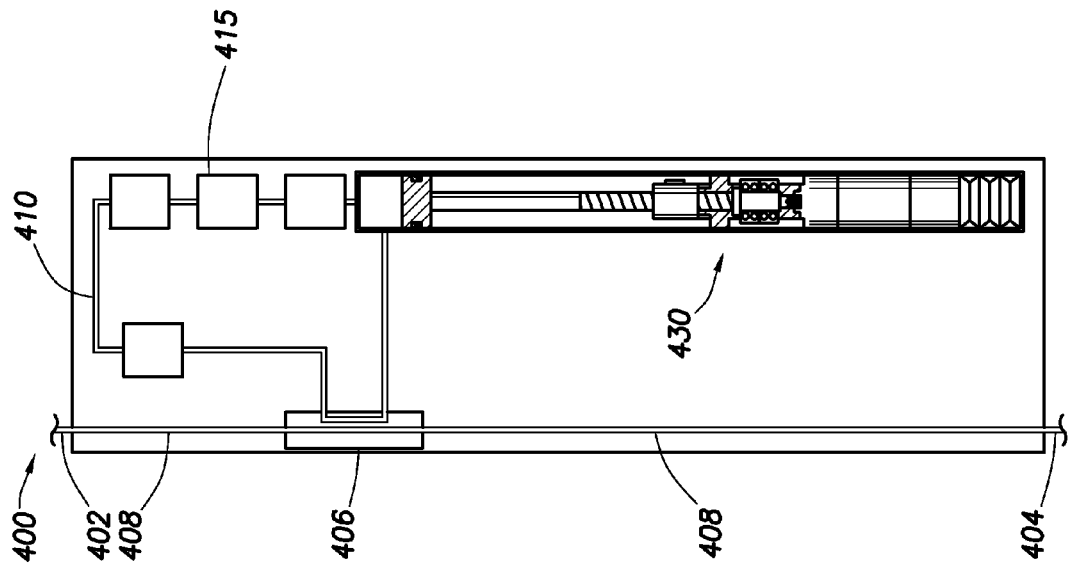
FIGS. 4A and 4B are sectional views of a portion of the phase transition measurement tool shown in FIG. 3.
Figure 4A:
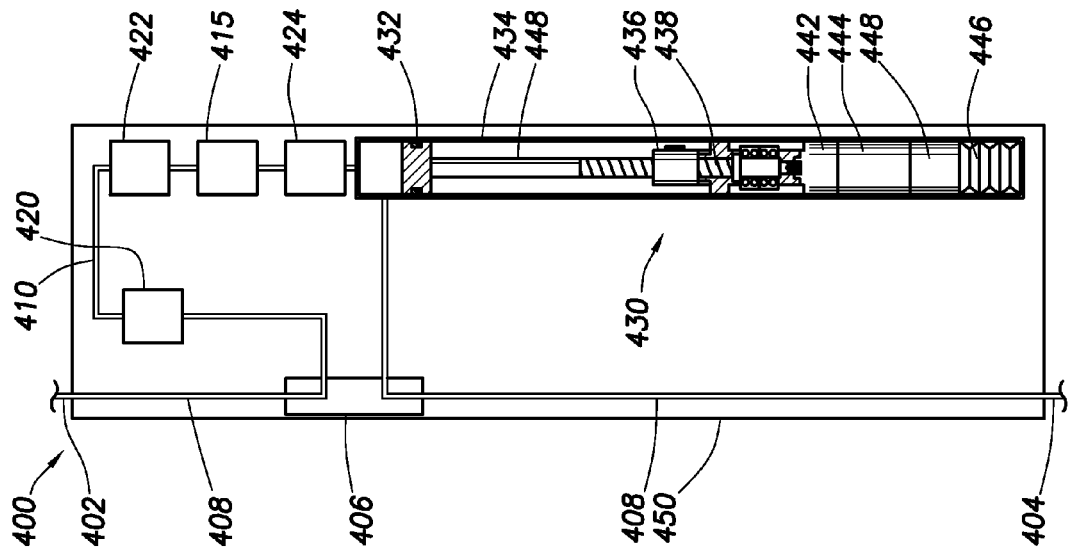

Turning to FIGS. 4A and 4B, sectional views of the fluid isolation and analysis tool 400 shown in FIG. 3 are depicted. In particular, the fluid isolation and analysis tool 400 may be configured to determine phase transition pressures of downhole fluids samples extracted from a subterranean formation F. The fluid isolation and analysis tool 400 may be used in a surface laboratory to analyze downhole fluid samples brought to the surface. Alternatively, the fluid isolation and analysis tool 400 may be used to implement the fluid isolation and analysis tool 226 (in FIG. 1) or the fluid isolation and analysis tool 120 (in FIG. 2A).

The fluid isolation and analysis tool 400 may include a downhole fluid inlet 402 for admitting a downhole fluid into the fluid isolation and analysis tool 400, and a downhole fluid outlet 404 for expulsing the downhole fluid from the fluid isolation and analysis tool 400. The inlet 402 and the outlet 404 are fluidly coupled to a flow line 408 of the fluid isolation and analysis tool 400. A four-port, two-position valve 406 may be used to selectively flow the downhole fluid admitted in the fluid isolation and analysis tool 400 through a test volume 410 (as shown in FIG. 4A), or seal a portion of the downhole fluid in the test volume 410 (as shown in FIG. 4B).

The fluid isolation and analysis tool 400 may comprise a pressure changing device 430. The pressure sensing device may comprise a sliding piston 432 configured to alter the pressure in the test volume 410. The piston 432 may be affixed to a ram 434, configured to reciprocate upon rotation of an electric motor 444 (e.g., a stepper motor). For example, an output shaft (not shown) of the motor 444 may be operatively coupled to a gear box 442. An output shaft 438 of the gear box may comprise a threaded portion that engages a nut 436 affixed to the ram 434.

The pressure changing device 430 may be disposed in a cavity containing pressurized hydraulic oil 448. When the fluid isolation and analysis tool 400 is part of a downhole tool (as shown in FIGS. 1, 2A and 2B), the pressure may be provided to the hydraulic oil 448 by the wellbore fluid via a bellows compensator 446 fluidly connected to the wellbore fluid. When the fluid isolation and analysis tool 400 is part of surface laboratory equipment, other pressure sources may be used in lieu of the bellows compensator 446. Further, the temperature of the test volume 410 may be maintained at a temperature close to the temperature of the subterranean formation from which the downhole fluid has been extracted. When the fluid isolation and analysis tool 400 is part of a downhole tool (as shown in FIGS. 1, 2A and 2B), the downhole fluid may be analyzed in situ, and therefore its temperature is usually close to the formation temperature. When the fluid isolation and analysis tool 400 is part of surface laboratory equipment, the temperature in a thermal enclosure 450 may be adjusted by using heaters among other means within the scope of the present disclosure.

The test volume 410 may be provided with a pressure gauge 420, configured to monitor the pressure of the downhole fluid in the test volume 410. The gauge 420 may also be configured to monitor the temperature of the downhole fluid in the test volume 410. The test volume 410 may optionally comprise one or more fluid sensor(s) 422 and 424 configured to measure a property of the downhole fluid. For example, the fluid sensor 422 may be implemented with a light scattering sensor, comprising a light source and a light detector configured to measure a light transmitted through the downhole fluid. The fluid sensor 424 may be implemented with a Density and/or Viscosity (DV) sensor. However, other sensors may further be implemented to measure fluid properties of the downhole fluid in the test volume 410. Further, the sensors may be arranged along the test volume 410 in various ways.

The test volume 410 may optionally be provided with a circulation pump 415. The circulation pump 415 may be used to agitate the downhole fluid in the test volume 410 by inducing a flow of downhole fluid in the test volume 410 and/or by mixing the downhole fluid, and thereby promote phase transition in the formation fluid. For example, a portion of the downhole fluid sealed in the test volume 410 may be circulated in the test volume 410, as apparent in FIG. 4B.

Turning to FIG. 5, an example graph 500 of a downhole fluid pressure as a function of time according to one or more aspects of the present disclosure is shown. The downhole fluid used in the example graph 500 is a volatile oil that has a known bubble point pressure of 4060 psi, independently determined in laboratory by the constant composition expansion (CCE) procedure. In particular, the graph 500 may illustrate pressure measurements obtained by the pressure sensor 420 (in FIG. 3) at a plurality of times, while the downhole fluid sealed in the test volume 410 (in FIG. 3) undergoes a depressurization via the PID controller implemented in the controller 465 (in FIG. 3). In the example graph 500, the targeted depressurization rate may be prescribed to be constant at 1000 psi/min. Other rates, however, are also within the scope of the present disclosure.

The graph 500 shows that pressure in the test volume decreases with time during depressurization. In particular, the pressure profile exhibits an initial ramp-up of depressurization rate for a period of about 50 seconds. After 50 seconds, the pressure profile exhibits a depressurization rate that is stable at the constant rate of 1000 psi/min. At about 367 seconds, the pressure profile exhibits an irregularity 502. At or near the irregularity 502, the characteristics of the pressure profile may change. For example, the pressure profile up to the irregularity 502 may vary according to the targeted depressurization rate. Then, the pressure profile past the irregularity 502 may vary according to a rate that deviates from the targeted depressurization rate. In this example, the irregularity 502 in the measured pressures may also be referred to as an anomaly in the measured pressures. After 367 seconds, the PID controller intends to drive depressurization rate back up to the targeted value of 1000 psi/min by increasing the motor speed. At about 410 seconds, the maximum speed of the stepper motor (1600 rpm) is reached and the depressurization from this point on is kept at the maximum speed until the end.

The time data points of the graph 500 may be analyzed to detect an occurrence of phase transition of the downhole fluid and/or to determine the phase transition pressure, that is in this example, the bubble point pressure Pb. Indeed, at a time when a phase transition occurs, (e.g., when gas bubbles emerge at the bubble point pressure Pb), the downhole fluid compressibility suddenly changes and the PID controller cannot immediately keep up with this sudden change. Therefore, the pressure profile (i.e., the measured pressures as a function of time) may exhibit the irregularity or anomaly 502 at the time when the phase transition occurs. The irregularity or anomaly 502 may thus be indicative of the phase transition occurrence (e.g., the onset of bubble emergence). Further, the downhole fluid pressure corresponding to the irregularity or anomaly 502, which is in this example 4061 psi, agrees very well with the bubble point pressure known from the value obtained using a CCE procedure.

It should be noted that in some cases, the irregularity or anomaly 502 may be apparent on a pressure profile such as the example graph 500. In other cases, the irregularity or anomaly 502 may be difficult to visualize and/or to detect on a pressure profile such as the example graph 500. Thus, it may be advantageous to determine parameters indicative of a curve irregularity or anomaly in measured pressures as a function of time, as further described in FIGS. 6A and/or 6B.

FIGS. 6A and 6B show graphs 510 and 520 of parameters indicative of a curve irregularity or anomaly in measured pressures as a function of time, such as in the graph 500 in FIG. 5. In particular, the graphs 510 and 520 may be used to monitor the plurality of measurements of the pressure of the downhole fluid obtained at each of a plurality of times associated with a pressure rate profile, and to determine at which of the plurality of times a corresponding one of the plurality of measurements deviates from the pressure rate profile.

Referring to FIG. 6A, the parameter indicative of the curve irregularity or anomaly in the measured pressures as a function of time includes an actual rate of the pressure change in the test volume. Indeed, the actual rate of the pressure change in the test volume may momentarily deviate from the targeted or prescribed rate at the time when the phase transition occurs. The deviation of the actual rate of the pressure change in the test volume from the targeted or prescribed rate value may be indicative of the phase transition occurrence. Thus, to detect the phase transition occurrence, the actual rate of the pressure change in the test volume may be compared to at least one prescribed rate associated with the pressure rate profile.

The graph 510 shows actual rates of the pressure change in the test volume as a function of time, determined using the pressure measurements as a function of time illustrated in FIG. 5. The actual rates of the pressure change may be determined by fitting a curve (e.g., a polynomial curve) to a portion of the measured pressures, and determining a curve slope. The fitting may be performed using a conventional least-squares algorithm such as the Savitzky-Golay filter (for example a second order filter), or using a robust iterative re-weighted least algorithm. As apparent in FIG. 6A, at about 367 seconds, an actual rate of the pressure change in the test volume deviates from the targeted rate of 1000 psi/min. The deviation time of 367 seconds agrees very well with the time at which the curve irregularity or anomaly 502 (in FIG. 5) occurs, and therefore may be used to detect the phase transition occurrence.

Referring to FIG. 6B, the parameter indicative of the curve irregularity or anomaly in the measured pressures as a function of time includes fitting error values or fitting residuals. Indeed, the pressure-versus-time data (in FIG. 5) may usually exhibit smooth curve portions, and therefore, the pressure-versus-time data may be well fitted by a smooth curve over a moving window. However, at and around a phase transition occurrence, the pressure-versus-time data may exhibit an irregularity or anomaly. The pressure-versus-time data may be relatively poorly fitted with the smooth curve over a time window overlapping the time at which the phase transition occurs. Thus, to detect the phase transition occurrence, the fitting error values or fitting residuals may be compared to a threshold value. At and around a phase transition occurrence, the fitting error values may be larger than the threshold value, while the fitting error values outside the phase transition occurrence may be lower than the threshold value.

The graph 520 shows fitting error values or fitting residuals of the pressure in the test volume as a function of time, determined using the pressure measurements as a function of time illustrated in FIG. 5. The fitting error values may be determined using a second order polynomial curve fitting over a 5 second window. The fitting error values may be computed by determining a difference between a measured pressure value at a given time and a value of the fitted curve at the given time. Since the difference between a measured pressure value at a given time and a value of the fitted curve at the given time can be positive or negative, an envelope of the difference was further computed using a Hilbert transform technique, as is well known in the art. As apparent in FIG. 6B, at about 367 seconds, the envelope of the fitting error values exhibits a peak which may be detected by using a threshold value. The peak time of 367 seconds agrees very well with the time at which the irregularity or anomaly 502 (in FIG. 5) occurs, and therefore may also be used to detect the phase transition occurrence.

While FIGS. 6A and 6B illustrate particular examples of methods that can be used to detect the time at which the irregularity or anomaly 502 (in FIG. 5) occurs, other methods may alternatively be used within the scope of the present disclosure. For examples, straight lines may be fitted to two or more portion of the pressure profile, and a straight line intersection may be determined.

Turning to FIG. 7, a graph 530 of a downhole fluid property as a function of time according to one or more aspects of the present disclosure is shown. The downhole fluid used in the example graph 530 is the same volatile oil used to generate the data shown in FIGS. 5, 6A and 6B. In particular, the graph 530 may illustrate measurements performed by the fluid sensor 422 in FIG. 3 while the downhole fluid sealed in the test volume 410 (in FIG. 3) undergoes a depressurization via the PID controller implemented in the controller 465 (in FIG. 3). In this example, the fluid sensor comprises a light source and a light detector configured to measure an intensity of light transmission through the downhole fluid.

The graph 530 shows a plurality of measurements of light transmission through the downhole fluid obtained during depressurization of the downhole fluid at the targeted depressurization rate of 1000 psi/min. Before about 367 seconds, the intensity value of light transmission through the downhole fluid is relatively high. After about 367 seconds, the intensity value of light transmission through the downhole fluid is relatively low. At about 367 seconds, when the dissolved gas in the downhole fluid forms bubbles, the light transmission level through the downhole fluid may exhibit a significant reduction, for example, caused by scattering of light by gas bubbles.

The time data points of the graph 530 may be analyzed to detect a presence of two phases in the downhole fluid, that is in this example, the onset of bubble emergence. Indeed, the reduction of light transmission level at about 367 second may be indicative of the emergence or presence of gas bubbles in the fluid. Thus, a plurality of parameter values indicative of light transmission through the downhole fluid may be measured as a function of time. At least first and second parameters values may be compared to detect a reduction of light transmission level. The reduction of light transmission level may be indicative of the emergence or presence of gas bubbles in the fluid. In this example, a first phase transition pressure derived from a pressure signature (i.e., from the irregularity or anomaly 502), and a second phase transition pressure derived from the variations of the light transmission level through the downhole fluid agree very well. However, they may differ in other examples.

Turning to FIG. 8, a flow chart of at least a portion of a method 600 of analyzing a downhole fluid according to one or more aspects of the present disclosure is shown. The order of execution of the steps depicted in the flow chart of FIG. 8 may be changed and/or some of the steps described may be combined, divided, rearranged, omitted, eliminated and/or implemented in other ways within the scope of the present disclosure.

At step 605, a downhole fluid sample extracted from a formation may be admitted into a test volume disposed in a fluid analysis tool (e.g., the wireline tool 200 in FIG. 1, the sampling-while-drilling device 150 in FIG. 2B, and/or the phase transition measurement tool 470 in FIGS. 3, 4A and 4B). In some cases, the downhole fluid sample may be brought to the surface and analyzed in a laboratory. In other cases, the downhole fluid samples may be analyzed in situ, using a fluid analysis tool lowered in a well drilled through the formation. In these cases, the fluid analysis tool may be used to extract formation fluid from the formation using the pump 221 (in FIG. 1) or the pump 175 (in FIG. 2B) until an acceptable or suitable level of contamination of the formation fluid by mud filtrate is achieved. For example, the contamination level may be monitored or determined from measurements performed by the fluid sensing unit 220 in FIG. 1 or the fluid sensing unit 170 (in FIG. 2B).

At step 610, the downhole fluid sample may be sealed in the fluid analysis tool, for example in a fluid isolation and analysis tool (e.g., 226 in FIG. 1, 120 in FIG. 2B, and/or 400 in FIGS. 3, 4A and 4B). For example, in reference to FIGS. 4A and 4B, the valve 406 may be switched from a position described in FIG. 4A, in which the test volume 410 may be fluidly coupled to the flow line 408, to a position described in FIG. 4B, in which the test volume 410 may be isolated from the flow line 408.

At step 615, the fluid analysis tool (e.g., the wireline tool 200 in FIG. 1, the sampling-while-drilling device 150 in FIG. 2B, and/or the phase transition measurement tool 470 in FIGS. 3, 4A and 4B) may be directed to induce or affect a targeted rate of change of the pressure of the downhole fluid. In other words, a pressure changing device may induce or affect a pressure change in the test volume based on a one or more prescribed rates, for example according to a predetermined pressure rate profile. When the downhole fluid is in single phase, the targeted or prescribed rate may be a depressurization rate (i.e., a reduction of the downhole fluid pressure). However, the targeted or prescribed rate may alternatively be a pressurization rate, for example when the downhole fluid contains multiple phases. In some cases, the pressure of the downhole fluid in the test volume may be depressurized at a constant targeted or prescribed rate, for example as further explained in the description of FIGS. 6 and 9A.

In one example, the pressure changing device may comprise an electric motor (e.g., the electric motor 444 in FIG. 4A) operatively coupled to a test volume (e.g., the test volume 410 in FIGS. 3, 4A and 4B) via a piston (e.g., the piston 432 in FIG. 4A) configured to alter the pressure in the test volume 410. A controller (e.g., the controller 465 in FIG. 3) may be communicatively coupled to a pressure sensor (e.g., the pressure sensor 420 in FIGS. 3, 4A and 4B), and may be configured to implement a feedback control of the motor using a proportional-integral-derivative controller (PID controller), for example as disclosed herein in relation to FIG. 3.

In another example, a fluid extraction pump (e.g., the fluid extraction pump 221 in FIG. 1, or the fluid extraction pump 175 in FIG. 2B) may be directed to induce or affect a targeted rate of change of the pressure of the downhole fluid in the fluid analysis tool. In this example, a pressure sensor (e.g., provided in the fluid sensing unit 220 in FIG. 1, or in the fluid sensing unit 170 in FIG. 2B) may be communicatively coupled to a downhole controller (e.g., provided in the downhole control system 212 in FIG. 1, or provided in the downhole control system 180 in FIG. 2B). The downhole controller may be configured to implement a feedback control of the motor using a proportional-integral-derivative controller (PID controller), for example as disclosed herein in FIG. 3. It should be appreciated that in this example, the downhole fluid may not be sealed in the fluid analysis tool, and may be essentially continuously extracted from the formation F (in FIGS. 1 and 2A) while the fluid analysis tool is directed to induce or affect a targeted rate of change of the pressure of the downhole fluid.

At step 620, the downhole fluid may optionally be agitated while the fluid analysis tool is directed to induce or affect a targeted rate of change of the pressure of the downhole fluid. In some cases, agitating the fluid may promote the phase transition in the downhole fluid, therefore, a more precise measurement of the phase transition pressure may be achieved. For example, a circulating pump (e.g., the circulating pump 415 in FIGS. 4A and 4B) may be used to induce a flow of downhole fluid in a test volume and/or to mix the downhole fluid in a test volume (e.g., the test volume 410 in FIGS. 4A and 4B), that has been sealed (such as shown in FIG. 4B).

At step 625, a plurality of measurements of the pressure of the downhole fluid corresponding to a plurality of times may be obtained. For example, the pressure measurements may be recorded or stored on a computer readable medium, and/or printed or displayed on a log, for example in the form of a graph similar to the graph 500 in FIG. 5.

In one example, the pressure measurements may be obtained using a pressure sensor (e.g., the pressure sensor 420 in FIGS. 3, 4A and 4B) fluidly coupled to a sealed test volume (e.g., the test volume 410 in FIGS. 3, 4A and 4B). In another example, the pressure measurements may be obtained using a pressure sensor provided in a fluid sensing unit through which the obtained fluid samples may flow (e.g., the fluid sensing unit 220 in FIG. 1, or the fluid sensing unit 170 in FIG. 2B).

At step 630, a plurality of measurements of light transmission through the downhole fluid may optionally be obtained. For example, light transmission levels may be recorded or stored on a computer readable medium, and/or printed or displayed on a log, for example in the form of a graph similar to the graph 530 in FIG. 7. In one example, the measurements of light transmission through the downhole fluid may be obtained using the fluid sensors 422 (in FIGS. 3, 4A and 4B). It should be appreciated however that other types of fluid properties may alternatively or additionally be obtained at step 630. For example, density and/or viscosity data, provided for example using the fluid sensor 424 (in FIGS. 4A and 4B), may be used.

At step 635, the pressure measurements obtained at step 625 may be monitored to determine at which time the pressure rate deviates from a targeted profile. In other words, a time at which an actual rate of the pressure change deviates from the prescribed rate may be determined at step 635. For example, a parameter indicative of a irregularity or anomaly in the measured pressures as a function of time (e.g., an actual rate of pressure change such as shown in FIG. 6A, and/or a fitting error value such as shown in FIG. 6B) may be determined, and the parameter indicative of the irregularity or anomaly may be compared to a threshold value. Based on the comparison, the time at which the pressure irregularity or anomaly occurs may be determined. In some cases, a processor (e.g., the processor 460 in FIG. 3) may be configured to determine the time at which an actual rate of the pressure change in the test volume deviates from the at least one prescribed rate using the measured pressures at the plurality of times.

At step 640, a presence of two phases in the downhole fluid may optionally be detected based on the light transmission measurements obtained at step 630. For example, the plurality of measurements of light transmission through the downhole fluid may be monitored. In particular, at least first and second parameter values indicative of light transmission through the downhole fluid may be measured. The first and second parameter values indicative of light transmission through the downhole fluid may then be compared to detect a reduction of light transmission level, for example as illustrated in FIG. 7. In some cases, a processor (e.g., the processor 460 in FIG. 3) may be configured to detect a presence of two phases in the downhole fluid using the downhole fluid properties measured by the fluid sensor. It should be appreciated however that the presence of two phases in the downhole fluid may be detected based on other types of fluid properties at step 640, for example, based on density and/or viscosity data.

At step 645, an occurrence of phase transition of the downhole fluid may be detected, based on at least one deviation time determined at step 635. In some cases, one deviation time may be determined at step 645, as shown in FIGS. 6A and 6B. In other cases, the techniques described in FIGS. 6A and 6B may generate two or more values for a deviation time. In these cases, the detection of the occurrence of phase transition of the downhole fluid may be based on the smaller of the two or more values for the deviation time, or on an average value of the two or more values for the deviation time. Optionally, the occurrence of phase transition of the downhole fluid may further be detected based on the presence of two phases in the downhole fluid detected at step 640. For example, the detection of the occurrence of phase transition of the downhole fluid may be based on the deviation time determined at step 635, and the time at which a reduction of light transmission level is detected at step 640. In some cases, a processor (e.g., the processor 460 in FIG. 3) may be configured to detect an occurrence of phase transition of the downhole fluid based on the deviation time determined at step 635.

At step 650, a phase transition pressure may be determined from the occurrence of phase transition detected at step 645, and at least a portion of the pressures measured at step 625. For example, the phase transition pressure may be the measured pressure of the downhole fluid corresponding to the detected occurrence of phase transition.

At step 655, a determination whether the test should be terminated may be made. For example, the fluid analysis tool may be directed to stop inducing or affecting the targeted rate of change of the pressure of the downhole fluid initiated at step 615. The fluid analysis tool may be directed to stop inducing or affecting the targeted rate of change of the pressure of the downhole fluid shortly after the occurrence of the phase transition of the downhole fluid has been detected at step 645. Thus, the duration of the test may be limited. In some cases, the test may continue. For example, after a depressurization, the downhole fluid may be pressurized. One method of pressurizing the downhole fluid may comprise performing one or more of the steps 615, 620, 625, 630, 635, 640, 645, 650 and 655. Thus, another determination of the downhole fluid phase transition pressure may be performed as the fluid analysis tool is directed to induce or affect one or more targeted rate of pressure increase of the downhole fluid.

The test may be terminated at step 655. For example, the downhole fluid may be pressurized to a pressure level that facilitates the opening of a valve configured to isolate the downhole fluid in the test volume (e.g., a pressure level that minimize the differential pressure across the valve 406 in FIGS. 4A and 4B). Further, the downhole fluid may be pressurized to a pressure that facilitates the downhole fluid recombination into a single phase fluid. The downhole fluid may be expulsed from the fluid analysis tool at step 660.

Figure 9:
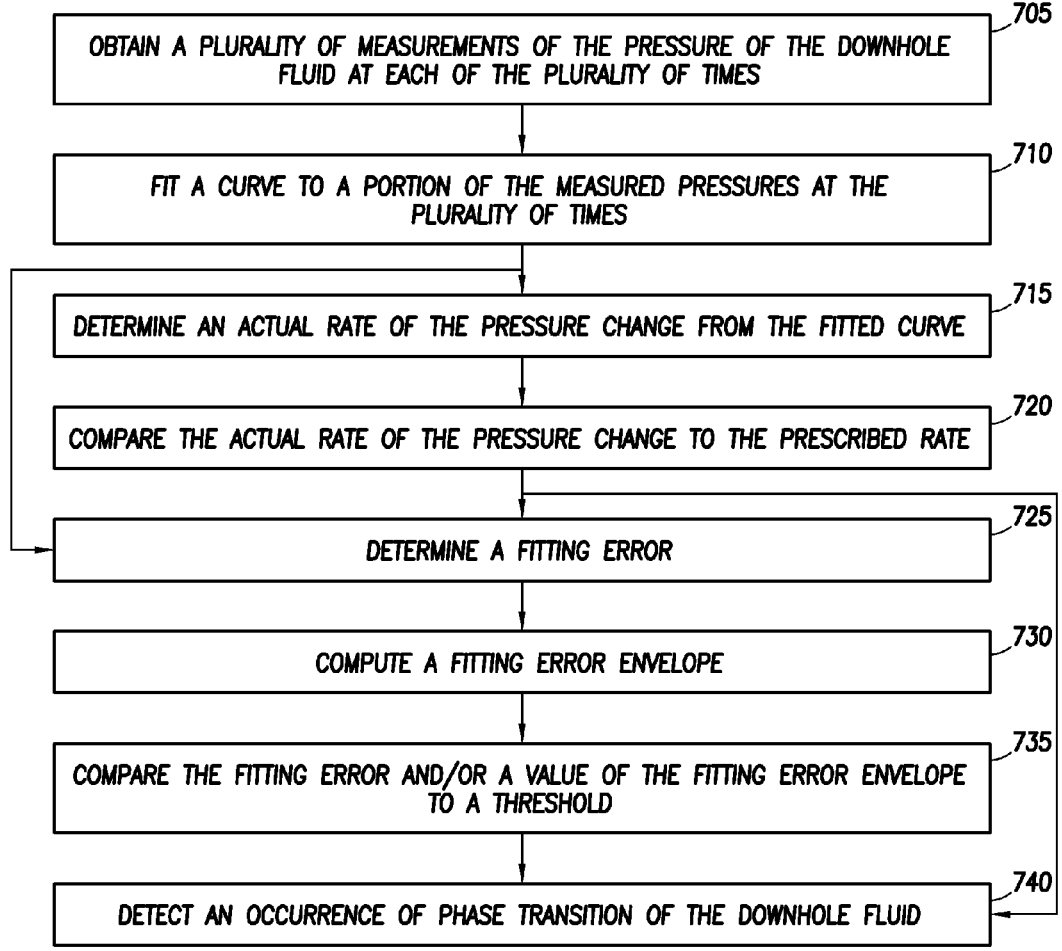
FIG. 9 is a flow chart of at least a portion of a method of determining parameters indicative of a curve irregularity in measured pressures as a function of time according to one or more aspects of the present disclosure.

Turning to FIG. 9, an example flow chart of at least a portion of a method 700 of determining parameters indicative of a curve irregularity or anomaly in measured pressures as a function of time is shown. The method 700 may be used to perform the operations described at the step 635 of FIG. 8. It should be appreciated that the order of execution of the steps depicted in the flow chart of FIG. 9 may be changed and/or some of the steps described may be combined, divided, rearranged, omitted, eliminated and/or implemented in other ways within the scope of the present disclosure.

At step 705, a plurality of measurements $p(t_0)$, $p(t_1)$, $p(t_2)$, ..., $p(t_n)$ of the pressure of the downhole fluid at each of a plurality of times may be obtained. For example, the plurality of measurements of the pressure of the downhole fluid may be obtained as described in step 625 in FIG. 8.

At step 710, a curve may be fitted to a portion of the measured pressures at the plurality of times. For example, a second order polynomial curve may be fitted to a 5 second moving window on the measured pressures. Thus, the fitting curve may be expressed as:

$$p(t_j) \approx a + b(t_j - t_i) + c(t_j - t_i)^2$$

where $t_i$ is the center of the moving window, and a, b, and c are the three unknown fitting parameters. The fitting parameters may be determined using a conventional least-squares algorithm such as the Savitzky-Golay filter (for example a second order filter), or using a robust iterative re-weighted least algorithm. After the operations associated with step 710 have been performed, the method 700 may optionally include steps 715, and 720, or continue with step 720, as further described below.

At step 715, an actual rate of the pressure change $y(t_j)$, may be determined from the fitted curve. For example, using the values of the fitting parameters determined at step 715, the actual rate of the pressure change may be determined at any time $t_j$ in the moving interval by:

$$y(t_j) = \frac{d}{dt} p(t_j) \approx b + 2c(t_j - t_i)$$

An example of a pressure rate curve $y(t_j)$ is shown in FIG. 6A.

At step 720, one or more actual rates of pressure change may be compared to the prescribed or targeted rate, for example $s(t_j)$. After the operations associated with step 720 have been performed, the method 700 may optionally include steps 725, 730, and 735, or continue with step 740, as further described below.

At step 725, one or more fitting error value(s) $\gamma(t_j)$ may be determined. For example, using the values of the fitting parameters determined at step 715, the fitting error value may be determined at any time $t_j$ in the moving interval by:

$$\gamma(t_j) = p(t_j) - [a + b(t_j - t_i) + c(t_j - t_i)^2]$$

At step 730, a fitting error envelope may be computed. For example, the envelope of the fitting error at a time $t_j$, $\overline{\omega}(t_j)$, may be computed by:

$$\overline{\omega}(t_j) = \sqrt{\gamma(t_j)^2 + \zeta(t_j)^2}$$

where $\zeta(t)$ is the Hilbert transform of the fitting error values $\gamma(t)$. An example of an error envelope curve $\bar{\omega}(t)$ is shown in FIG. 6B.

At step 735, a fitting error value, such as the fitting error value $\gamma(t_j)$ and/or the envelope of the fitting error $\bar{\omega}(t_j)$ may be compared to a threshold value. The threshold value may be selected such that a fitting error value above the threshold value may be indicative of an irregularity or anomaly in the measured pressures as a function of time in the moving window.

At step 740, an occurrence of a phase transition of the downhole fluid may be detected based on the comparisons performed at steps 720 and/or 735. For example, the occurrence of the phase transition of the downhole fluid may be detected as described in step 645 in FIG. 8.

In view of all of the above and FIGS. 1 to 9, it should be readily apparent to those skilled in the art that the present disclosure provides a method of analyzing a downhole fluid, comprising admitting downhole fluid into a fluid analysis tool, directing the fluid analysis tool to affect a targeted rate of change of the pressure of the downhole fluid in the fluid analysis tool, obtaining a plurality of measurements of the pressure of the downhole fluid at each of a plurality of times associated with the targeted rate of change of the pressure of the downhole fluid, monitoring the plurality of measurements to determine at which of the plurality of times a corresponding one of the plurality of measurements deviates from the targeted rate of change of the pressure of the downhole fluid, and detecting an occurrence of phase transition of the downhole fluid based on the time at which the corresponding one of the plurality of measurements deviates from the targeted rate of change of the pressure of the downhole fluid. The method may further comprise determining a phase transition pressure from the detected occurrence of phase transition, and at least a portion of the obtained plurality of measurements of the pressure of the downhole fluid. The method may further comprise sealing the downhole fluid in the fluid analysis tool. The method may further comprise agitating the downhole fluid in the fluid analysis tool. Agitating the downhole fluid in the fluid analysis tool may comprise circulating the downhole fluid in the fluid analysis tool. The method may further comprise detecting a presence of two phases in the downhole fluid. Detecting the presence of two phases in the downhole fluid may comprise obtaining a plurality of measurements of light transmission through the downhole fluid, and monitoring the plurality of light transmission through the downhole fluid to detect a reduction of light transmission level. Directing the fluid analysis tool to affect the targeted rate of change of the pressure of the downhole fluid in the fluid analysis tool may comprise directing the fluid analysis tool to depressurize the downhole fluid according to a constant rate of change of the pressure of the downhole fluid. Directing the fluid analysis tool to affect the targeted rate of change of the pressure of the downhole fluid in the fluid analysis tool may comprise actuating an electric motor operatively coupled to the fluid analysis tool. Monitoring the plurality of measurements to determine at which of the plurality of times a corresponding one of the plurality of measurements deviates from the targeted rate of change of the pressure of the downhole fluid may comprise fitting a curve to a portion of the obtained plurality of measurements of the pressure of the downhole fluid, determining a fitting error, and comparing the fitting error to a threshold. Monitoring the plurality of measurements to determine at which of the plurality of times a corresponding one of the plurality of measurements deviates from targeted rate of change of the pressure of the downhole fluid may comprise determining an actual rate of change of the pressure of the downhole fluid, and comparing the actual rate of change of the pressure of the downhole fluid with the targeted rate of change of the pressure of the downhole fluid. The method may further comprise lowering the fluid analysis tool in a wellbore penetrating a subterranean formation using one of a wireline cable, a drill string, and a tubing.

The present disclosure also provides a method of analyzing a downhole fluid, comprising admitting the downhole fluid in a test volume, controllably inducing a pressure change in the test volume based on at least one prescribed rate, measuring pressures in the test volume at a plurality of times, determining a time at which an actual rate of the pressure change in the test volume deviates from the at least one prescribed rate using the pressures measured at the plurality of times, and detecting an occurrence of phase transition of the downhole fluid based on the determined time. The method may further comprise determining a phase transition pressure from the detected occurrence of phase transition, and at least a portion of the pressures measured at the plurality of times. The method may further comprise sealing the downhole fluid in the test volume. Controllably inducing the pressure change in the test volume based on the at least one prescribed rate may comprise controlling an expansion of the sealed test volume based on the pressures measured at the plurality of times. The method may further comprise agitating the downhole fluid in the test volume. Agitating the downhole fluid in the test volume may comprise flowing the downhole fluid in the test volume using a circulating pump. The method may further comprise detecting a presence of two phases in the downhole fluid. Detecting the presence of two phases in the downhole fluid may comprise measuring first and second parameter values indicative of light transmission through the downhole fluid, and comparing the first and second parameter values indicative of light transmission through the downhole fluid. Controllably inducing the pressure change in the test volume based on the at least one prescribed rate may comprise depressurizing the test volume based on a constant rate. Controllably inducing the pressure change in the test volume based on the at least one prescribed rate may comprise actuating an electric motor operatively coupled to the test volume via a piston configured to alter the pressure in the test volume. Determining the time at which the actual rate of the pressure change in the test volume deviates from the at least one prescribed rate may comprise determining a parameter indicative of an irregularity in the measured pressures as a function of time, and comparing the parameter indicative of the irregularity to a threshold value. Determining the parameter indicative of the irregularity in the measured pressures as a function of time may comprise fitting a curve to a portion of the measured pressures at the plurality of times, and determining a fitting error. Determining the fitting error may comprise determining a difference between a measured pressure and a value of the fitted curve. The method may further comprise determining an actual rate of pressure change in the test volume based on the fitted curve, and comparing the actual rate of the pressure change in the test volume to the at least one prescribed rate. Determining the parameter indicative of the irregularity in the measured pressures as a function of time may comprise determining an actual rate of the pressure change in the test volume. Comparing the parameter indicative of the irregularity to the threshold value may comprise comparing the actual rate of the pressure change in the test volume to the at least one prescribed rate. Determining the actual rate of the pressure change in the test volume may comprise fitting a curve to a portion of the measured pressures at the plurality of times, and determining a curve slope. The method may further comprise lowering a downhole tool in a wellbore penetrating a subterranean formation, the test volume being disposed in the downhole tool, and wherein controllably inducing the pressure change in the test volume may be performed by the downhole tool in situ. Lowering the downhole tool in the wellbore may be performed using one of a wireline cable, a drill string, and a tubing.

The present disclosure also provides a fluid analysis tool, comprising a test volume configured to admit a downhole fluid therein, a pressure sensor configured to measure pressures in the test volume at a plurality of times, a pressure changing device configured to controllably induce a pressure change in the test volume based on at least one prescribed rate, and a processor configured to determine a time at which an actual rate of the pressure change in the test volume deviates from the at least one prescribed rate using the measured pressures at the plurality of times, and to detect an occurrence of phase transition of the downhole fluid based on the determined time. The fluid analysis tool may further comprise one or more valves configured to seal the downhole fluid in the test volume. The fluid analysis tool may further comprise a circulating pump configured to agitate the downhole fluid in test volume. The fluid analysis tool may further comprise a fluid sensor configured to measure a property of the downhole fluid. The fluid sensor may comprise a light detector configured to measure a light transmission through the downhole fluid. The processor may be further configured to detect a presence of two phases in the downhole fluid using the downhole fluid properties measured by the fluid sensor. The pressure changing device may comprise an electric motor operatively coupled to the test volume via a piston configured to alter the pressure in the test volume. The pressure changing device may comprise a controller communicatively coupled to the pressure sensor, and configured to induce the pressure change in the test volume based on the measured pressures in the test volume. The test volume may be disposed in a downhole tool, the downhole tool being configured to be lowered in a wellbore penetrating a subterranean formation. The downhole tool may be configured to be lowered in the wellbore using one of a wireline cable, a drill string, and a tubing.

The present disclosure also provides a method of analyzing a downhole fluid, comprising lowering a downhole tool in a wellbore penetrating a subterranean formation, the downhole tool comprising a test volume disposed therein, admitting the downhole fluid in the test volume, sealing the downhole fluid in the test volume, measuring pressures in the test volume at a plurality of times, controllably inducing a pressure change in the test volume based on a constant depressurizing rate, determining actual rates of the pressure change in the test volume using the measured pressures, comparing the actual rates of the pressure change in the test volume with the constant depressurizing rate, determining a time at which one of the actual rates of the pressure change in the test volume deviates from the constant depressurizing rate based on the comparison, and determining a phase transition pressure based on the determined time and at least a portion of the pressures measured at the plurality of times.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of analyzing a downhole fluid, comprising:
admitting the downhole fluid in a test volume;
controllably inducing a pressure change in the test volume based on at least one prescribed rate;
measuring pressures in the test volume at a plurality of times;
determining a time at which an actual rate of the pressure change in the test volume deviates from the at least one prescribed rate using the pressures measured at the plurality of times; and
detecting an occurrence of phase transition of the downhole fluid based on the determined time.

2. The method of claim 1 further comprising determining a phase transition pressure from the detected occurrence of phase transition and at least a portion of the pressures measured at the plurality of times.

3. The method of claim 1 further comprising sealing the downhole fluid in the test volume, wherein controllably inducing the pressure change in the test volume based on the at least one prescribed rate comprises controlling an expansion of the sealed test volume based on the pressures measured at the plurality of times.

4. The method of claim 1 further comprising agitating the downhole fluid in the test volume.

5. The method of claim 1 further comprising detecting a presence of two phases in the downhole fluid.

6. The method of claim 5 wherein detecting the presence of two phases in the downhole fluid comprises measuring and comparing first and second parameter values indicative of light transmission through the downhole fluid.

7. The method of claim 1 wherein controllably inducing the pressure change in the test volume based on the at least one prescribed rate comprises depressurizing the test volume based on a constant rate.

8. The method of claim 1 wherein controllably inducing the pressure change in the test volume based on the at least one prescribed rate comprises actuating an electric motor operatively coupled to the test volume via a piston configured to alter the pressure in the test volume.

9. The method of claim 1 wherein determining the time at which the actual rate of the pressure change in the test volume deviates from the at least one prescribed rate comprises:
determining a parameter indicative of an irregularity in the measured pressures as a function of time; and
comparing the parameter indicative of the irregularity to a threshold value.

10. The method of claim 9 wherein determining the parameter indicative of the irregularity in the measured pressures as a function of time comprises fitting a curve to a portion of the measured pressures at the plurality of times and determining a fitting error, wherein determining the fitting error comprises determining a difference between a measured pressure and a value of the fitted curve.

11. The method of claim 9 wherein determining the parameter indicative of the irregularity in the measured pressures as a function of time comprises determining an actual rate of the pressure change in the test volume.

12. The method of claim 11 wherein comparing the parameter indicative of the irregularity to the threshold value comprises comparing the actual rate of the pressure change in the test volume to the at least one prescribed rate.

13. The method of claim 11 wherein determining the actual rate of the pressure change in the test volume comprises fitting a curve to a portion of the measured pressures at the plurality of times, and determining a curve slope.

14. The method of claim 1 further comprising lowering a downhole tool in a wellbore penetrating a subterranean formation using one of a wireline cable, a drill string, and a tubing, the test volume being disposed in the downhole tool, and wherein controllably inducing the pressure change in the test volume is performed by the downhole tool in situ.

15. A fluid analysis tool, comprising:
a test volume configured to admit a downhole fluid therein;
a pressure sensor configured to measure pressures in the test volume at a plurality of times;
a pressure changing device configured to controllably induce a pressure change in the test volume based on at least one prescribed rate; and
a processor configured to determine a time at which an actual rate of the pressure change in the test volume deviates from the at least one prescribed rate using the measured pressures at the plurality of times, and to detect an occurrence of phase transition of the downhole fluid based on the determined time.

16. The fluid analysis tool of claim 15 further comprising a fluid sensor configured to measure a property of the downhole fluid.

17. The fluid analysis tool of claim 16 wherein the fluid sensor comprises a light detector configured to measure a light transmission through the downhole fluid.

18. The fluid analysis tool of claim 15 wherein the pressure changing device comprises an electric motor operatively coupled to the test volume via a piston configured to alter the pressure in the test volume.

19. The fluid analysis tool of claim 15 wherein the pressure changing device comprises a controller communicatively coupled to the pressure sensor and configured to induce the pressure change in the test volume based on the measured pressures in the test volume.

20. A method of analyzing a downhole fluid, comprising:
lowering a downhole tool in a wellbore penetrating a subterranean formation, the downhole tool comprising a test volume disposed therein;
admitting the downhole fluid in the test volume;
sealing the downhole fluid in the test volume;
measuring pressures in the test volume at a plurality of times;
controllably inducing a pressure change in the test volume based on a constant depressurizing rate;
determining actual rates of the pressure change in the test volume using the measured pressures;
comparing the actual rates of the pressure change in the test volume with the constant depressurizing rate;
determining a time at which one of the actual rates of the pressure change in the test volume deviates from the constant depressurizing rate based on the comparison; and
determining a phase transition pressure based on the determined time and at least a portion of the pressures measured at the plurality of times.

\* \* \* \* \*